US008877230B2

(12) United States Patent
Mattern

(10) Patent No.: US 8,877,230 B2
(45) Date of Patent: *Nov. 4, 2014

(54) CONTROLLED RELEASE DELIVERY SYSTEM FOR NASAL APPLICATIONS

(75) Inventor: Claudia Mattern, Stans (CH)

(73) Assignee: Mattern Pharma AG, Vaduz (LI)

( * ) Notice: Subject to any disclaimer, the term of this patent is extended or adjusted under 35 U.S.C. 154(b) by 0 days.

This patent is subject to a terminal disclaimer.

(21) Appl. No.: 13/316,494

(22) Filed: Dec. 10, 2011

(65) Prior Publication Data

US 2012/0083480 A1 Apr. 5, 2012

Related U.S. Application Data

(60) Division of application No. 13/194,928, filed on Jul. 30, 2011, which is a continuation of application No. 10/772,964, filed on Feb. 4, 2004, now abandoned.

(30) Foreign Application Priority Data

Nov. 11, 2003 (EP) .................................. 03025769

(51) Int. Cl.
| | |
|---|---|
| A61F 13/00 | (2006.01) |
| A61K 31/56 | (2006.01) |
| A61K 31/568 | (2006.01) |
| A61K 9/00 | (2006.01) |

(52) U.S. Cl.
CPC .............. *A61K 9/0043* (2013.01); *A61K 31/568* (2013.01)
USPC ........................................ 424/434; 514/178

(58) Field of Classification Search
CPC ............ A61K 31/568; A61K 19/0043; A61K 31/565; A61P 5/26

USPC ........................................... 424/434; 514/178
See application file for complete search history.

(56) References Cited

U.S. PATENT DOCUMENTS

| | | |
|---|---|---|
| 4,071,623 A | 1/1978 | Van Der Vies |
| 4,083,973 A | 4/1978 | Van Der Vies |
| 4,315,925 A | 2/1982 | Hussain et al. |
| 4,581,225 A | 4/1986 | Su et al. |
| 4,752,425 A | 6/1988 | Martin et al. |
| 5,049,387 A | 9/1991 | Amkraut |
| 5,397,771 A | 3/1995 | Bechgaard et al. |

(Continued)

FOREIGN PATENT DOCUMENTS

| | | |
|---|---|---|
| DE | 943792 | 6/1956 |
| DE | 1569286 | 10/1976 |

(Continued)

OTHER PUBLICATIONS

Dondeti et al., "Bioadhesive and formulation parameter affecting nasal absorption", International Journal of Pharmaceutics, 127 (1996) 115-133.

(Continued)

*Primary Examiner* — Aradhana Sasan
(74) *Attorney, Agent, or Firm* — Foley & Lardner LLP

(57) ABSTRACT

This invention relates to a pernasally administrable preparation for the controlled release of sexual hormones to the systemic circulation, in particular to a formulation which enables its active ingredient to be absorbed in a sustained manner providing a better bioavailability at very low doses and longer duration of action.

23 Claims, 1 Drawing Sheet

(56) References Cited

U.S. PATENT DOCUMENTS

| | | | |
|---|---|---|---|
| 5,455,286 A | 10/1995 | Amidon et al. | |
| 5,514,673 A | 5/1996 | Heckenmuller et al. | |
| 5,635,203 A | 6/1997 | Gale et al. | |
| 5,645,856 A | 7/1997 | Lacy et al. | |
| 5,747,058 A | 5/1998 | Tipton et al. | |
| 5,756,071 A * | 5/1998 | Mattern et al. | 424/45 |
| 5,863,554 A | 1/1999 | Illum | |
| 5,877,216 A | 3/1999 | Place et al. | |
| 5,897,894 A | 4/1999 | Glass | |
| 6,248,363 B1 | 6/2001 | Patel et al. | |
| 6,287,588 B1 | 9/2001 | Shih et al. | |
| 6,309,663 B1 | 10/2001 | Patel et al. | |
| 6,310,089 B1 | 10/2001 | Watts et al. | |
| 6,432,440 B1 | 8/2002 | Watts et al. | |
| 6,451,339 B2 | 9/2002 | Patel et al. | |
| 6,720,001 B2 | 4/2004 | Chen et al. | |
| 6,761,903 B2 | 7/2004 | Chen et al. | |
| 6,833,478 B2 | 12/2004 | Bottaro et al. | |
| 6,958,142 B2 | 10/2005 | Daniels et al. | |
| 7,186,706 B2 | 3/2007 | Rosario-Jansen et al. | |
| 7,198,801 B2 | 4/2007 | Carrara et al. | |
| 7,470,433 B2 | 12/2008 | Carrara et al. | |
| 2001/0055569 A1 | 12/2001 | Davis et al. | |
| 2002/0136752 A1 | 9/2002 | Whittle et al. | |
| 2002/0198136 A1 | 12/2002 | Mak et al. | |
| 2003/0153540 A1 | 8/2003 | Rosario-Jansen et al. | |
| 2004/0005275 A1 | 1/2004 | Gizurarson et al. | |
| 2004/0022738 A1 | 2/2004 | Pike et al. | |
| 2004/0022739 A1 | 2/2004 | Daniels et al. | |
| 2005/0100564 A1 | 5/2005 | Mattern | |
| 2005/0152956 A1 | 7/2005 | Dudley | |
| 2005/0153946 A1 | 7/2005 | Hirsh et al. | |
| 2005/0187188 A1 | 8/2005 | Stein et al. | |
| 2006/0008420 A1 | 1/2006 | Daniels et al. | |
| 2006/0147385 A1 | 7/2006 | Pike et al. | |
| 2006/0210622 A1 | 9/2006 | Pace et al. | |
| 2006/0211664 A1 | 9/2006 | Dudley | |
| 2007/0149454 A1 | 6/2007 | Mattern | |
| 2007/0190120 A1 | 8/2007 | Rosario-Jansen et al. | |
| 2009/0227550 A1 | 9/2009 | Mattern | |
| 2009/0318398 A1 | 12/2009 | Dudley et al. | |
| 2010/0136105 A1 | 6/2010 | Chen et al. | |
| 2010/0311707 A1 | 12/2010 | Mattern | |
| 2011/0009318 A1 | 1/2011 | White et al. | |
| 2011/0195114 A1 | 8/2011 | Carrara et al. | |
| 2011/0245215 A1 | 10/2011 | Carrara et al. | |
| 2012/0009249 A1 | 1/2012 | Mattern | |
| 2012/0009250 A1 | 1/2012 | Mattern | |
| 2012/0058176 A1* | 3/2012 | Mattern | 424/450 |
| 2012/0083480 A1 | 4/2012 | Mattern | |
| 2012/0277202 A1 | 11/2012 | Mattern | |
| 2012/0297730 A1 | 11/2012 | Mattern | |

FOREIGN PATENT DOCUMENTS

| | | |
|---|---|---|
| EP | 0 160 501 | 11/1985 |
| EP | 0349091 | 1/1990 |
| EP | 1530965 | 5/2005 |
| GB | 1 569 286 | 6/1980 |
| GB | 2 237 510 | 5/1991 |
| JP | 0106716 | 1/1989 |
| JP | 2003/509453 | 3/2003 |
| TW | 175318 | 12/1991 |
| WO | WO 95/20945 A1 | 8/1995 |
| WO | WO 97/40823 | 11/1997 |
| WO | WO 98/47535 | 10/1998 |
| WO | WO 00/59512 | 10/2000 |
| WO | WO 01/41732 A1 | 6/2001 |
| WO | WO 01/95888 A1 | 12/2001 |
| WO | WO 03/063833 A1 | 8/2003 |

OTHER PUBLICATIONS

Hussain et al., "Testosterone 17 β-N, N-Dimethylglycinate Hydrochloride: A Prodrug with a Potential for Nasal Delivery of Testosterone", Journal of Pharmaceutical Sciences, vol. 91, No. 3, Mar. 2002, pp. 785-789.

Ko et al., "Emulsion formulations of testosterone for nasal administration", J. Microencapsulation, 1998, vol. 15, No. 2, pp. 197-205.

Cicinelli et al., "Progesterone administration by nasal spray", Fertility and Sterility, vol. 56, No. 1, Jul. 1991, pp. 139-141.

Cicinelli et al., "Nasally-administered progesterone: comparison of ointment and spray formulations", Elsevier Scientific Publishers Ireland Ltd., 13 (1991), pp. 313-317.

Cicinelli et al., "Progesterone administration by nasal spray in menopausal women: comparison between two different spray formulations", Gynecol. Endocrinol., 6(1992), pp. 247-251.

Cicinelli et al., "Nasal spray administration of unmodified progesterone: evaluation of progesterone serum levels with three different radioimmunoassay techniques", Maturitas Journal of the Climacteric & Postmenopause, 19(1994), pp. 43-52.

Steege et al., "Bioavailability of nasally administered progesterone", Fertility and Sterility, vol. 46, No. 4, 1986, pp. 727-729.

Provasi et al., "Nasal delivery progesterone powder formulations comparison with oral administration", Boll. Chim. Farmaceutico, Ann 132, n. 10 (1993), pp. 402-404.

Notice of Allowance issued on Jul. 5, 2013 by the Examiner in U.S. Appl. No. 13/194,928 (US 2012/0009250).

Notice of Allowance issued on Mar. 25, 2013 by the Examiner in U.S. Appl. No. 13/194,928 (US 2012/0009250).

Office Action issued on Nov. 5, 2012 by the Examiner in U.S. Appl. No. 13/194,928 (US 2012/0009250).

Office Action issued on Feb. 15, 2012 by the Examiner in U.S. Appl. No. 13/194,928 (US 2012/0009250).

Office Action issued on Nov. 9, 2011 by the Examiner in U.S. Appl. No. 13/194,928 (US 2012/0009250).

Office Action issued on Jan. 13, 2012 by the Examiner in U.S. Appl. No. 12/796,165 (US 2010/0311707).

Office Action issued on Nov. 16, 2009 by the Examiner in U.S. Appl. No. 11/560,187 (US 2007/0149454).

Office Action issued on Mar. 18, 2009 by the Examiner in U.S. Appl. No. 11/560,187 (US 2007/0149454).

Office Action issued on Oct. 29, 2008 by the Examiner in U.S. Appl. No. 11/560,187 (US 2007/0149454).

Office Action issued on Aug. 20, 2008 by the Examiner in U.S. Appl. No. 11/560,187 (US 2007/0149454).

Office Action issued on Feb. 5, 2008 by the Examiner in U.S. Appl. No. 11/560,187 (US 2007/0149454).

Office Action issued on Sep. 14, 2007 by the Examiner in U.S. Appl. No. 11/560,187 (US 2007/0149454).

Office Action issued on Jul. 8, 2010 by the Examiner in U.S. Appl. No. 10/772,964 (US 2005/0100564).

Office Action issued on Sep. 29, 2009 by the Examiner in U.S. Appl. No. 10/772,964 (US 2005/0100564).

Office Action issued on Jan. 15, 2009 by the Examiner in U.S. Appl. No. 10/772,964 (US 2005/0100564).

Office Action issued on May 5, 2008 by the Examiner in U.S. Appl. No. 10/772,964 (US 2005/0100564).

Office Action issued on Mar. 17, 2008 by the Examiner in U.S. Appl. No. 10/772,964 (US 2005/0100564).

Office Action issued on Apr. 4, 2007 by the Examiner in U.S. Appl. No. 10/772,964 (US 2005/0100564).

Office Action issued on Jul. 3, 2012 by the Examiner in U.S. Appl. No. 13/316,494 (US 2012/0083480).

Office Action issued on Oct. 19, 2012 by the Examiner in U.S. Appl. No. 13/567,878 (US 2012/0297730)).

Office Action issued on Jul. 3, 2012 by the Examiner in U.S. Appl. No. 13/194,853 (US 2012/0058176).

Office Action issued on Aug. 14, 2012 by the Examiner in U.S. Appl. No. 13/194,853 (US 2012/0058176).

Office Action issued on Mar. 22, 2013 by the Examiner in U.S. Appl. No. 13/194,853 (US 2012/0058176).

Office Action issued on Jun. 5, 2013 by the Examiner in U.S. Appl. No. 13/547,774 (US 2012/0277202).

International Search Report issued on Dec. 21, 2007 in application No. PCT/EP2007/008409 (corresponding to US 2012/0009249).

(56) References Cited

OTHER PUBLICATIONS

Mattern et al., "Testosterone supplementation for hypogonadal men by the nasal route," The Aging Male, vol. 11, No. 4, pp. 171-178, Dec. 2008.

Banks et al., "Delivery of testosterone to the brain by intranasal administration: Comparison to intravenous testosterone," Journal of Drug Targeting, vol. 17, No. 2, pp. 1-7, Dec. 16, 2008.

Danner et al., "Androgen Substitution with Testosterone Containing Nasal Drops," International Journal of Andrology, vol. 3, No. 4, pp. 429-435, 1980.

Jung et al., "Prolonged delivery of nicotine in rats via nasal administration of proliposomes," Journal of Controlled Release, vol. 66, pp. 73-79, 2000.

Ohman et al., "17β-Estradiol Levels in Blood and Cerebrospinal Fluid After Ocular and Nasal Administration in Women and Female Rhesus Monkeys (*Macaca mulatta*)," Contraception, vol. 22, No. 4, pp. 349-358, Oct. 1980.

Skipor et al., "Local transport of testosterone from the nasal mucosa to the carotid blood and the brain in the pig," Polish Veterinary Sciences, vol. 3, No. 1, pp. 19-22, 2000.

Hussain et al., "Intranasal Drug Delivery," Advanced Drug Delivery Reviews, vol. 29, pp. 39-49, 1998.

Kumar et al., "Pharmacokinetics of progesterone after its administration to ovariectomized rhesus monkeys by injection, infusion, or nasal spraying," Proc. Natl. Acad. Sci. USA, vol. 79, pp. 4185-4189, Jul. 1982.

David et al., "Bioavailability of progesterone enhanced by intranasal spraying," Experientia, vol. 37, pp. 533-534, 1981.

Wattanakumtornkul et al., "Intranasal hormone replacement therapy," Menopause: The Journal of The North American Menopause Society, vol. 10, No. 1, pp. 88-98, 2003.

Hussain et al., "Nasal Absorption of Propranolol from Different Dosage Forms by Rats and Dogs," Journal of Pharmaceutical Sciences, vol. 69, No. 12, pp. 1411-1413, Dec. 1980.

Patent Abstracts of Japan, Tanabe Seiyaku Co., Ltd., "Dopamine Nasal Administration Preparation," JP 01-160916, Jun. 23, 1989.

European Search Report issued on Apr. 22, 2004 in application No. EP 03 02 5769.

International Search Report issued on Mar. 31, 2005 in application No. PCT/EP2004/012122.

Taiwanese Search Report issued Jan. 2006 in application No. 093129982.

Mattern et al., "Development of a drug formulation for nasal administration of a testosterone precursor and test of its bioavailability," First World Congress on Aging Male, Geneva, Switzerland, 1998, Abstract.

Häcker et al., "Androgenic substitution for the ageing male by nasal administraton of a precursor of testosterone," First World Congress on Aging Male, Geneva, Switzerland, 1998, Abstract.

Müller et al., "Androgenic deficiencies of the ageing male and psychophysiological performance—test system for clinical diagnosis," First World Congress on Aging Male, Geneva, Switzerland, 1998, Abstract.

Nogueira et al., "In-Vivo monitoring of neostriatal dopamine activity after nasal drug administration in the rat: relevance to Parkinson's Disease and addiction," Neuroscience Meeting, San Diego, California, 1995, Abstract.

Topic et al., "Evidence for antidepressant-like action of intranasal application of testosterone," CINP Biennial International Congress, Munich, Germany, Jul. 13-17, 2008, Abstract.

Provasi et al., "Nasal delivery progesterone powder formulations comparison with oral administration," Bol. Chim. Farmaceutico, Anno 132—n. 10 poster, 1993.

Corbo et al., "Nasal delivery of progestational steroids in ovariectomized rabbits. II. Effect of penetrant hydrophilicity," International Journal of Pharmaceutics, vol. 50, pp. 253-260, 1989.

Cicnelli et al., "Nasally-administered progesterone: comparison of ointment and spray formulations," Maturitas, vol. 13, pp. 313-317, 1991.

Cicinelli et al., "Administration of unmodified progesterone by nasal spray in fertile women," Gynecol. Endocrinol., vol. 9, pp. 289-293, 1995.

Hussain et al., "Nasal Absorption of Testosterone in Rats," Journal of Pharmaceutical Sciences, vol. 73, No. 9, pp. 1300-1301, Sep. 1984.

Marynick et al., "Studies on the Transfer of Steroid Hormones Across the Blood-Cerebrospinal Fluid Barrier in the Rhesus Monkey," Endo, vol. 99, No. 2, pp. 400-405, 1976.

\* cited by examiner

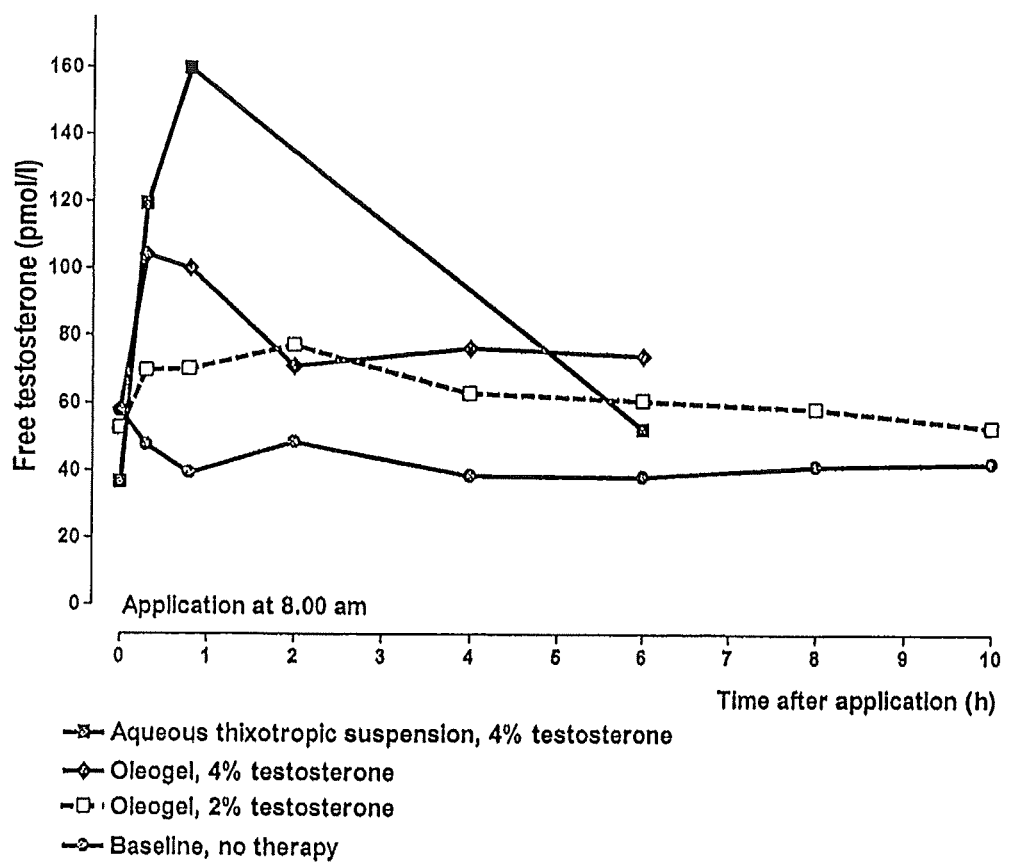

CONTROLLED RELEASE DELIVERY SYSTEM FOR NASAL APPLICATIONS

CROSS-REFERENCE TO RELATED APPLICATIONS

This application is a divisional of U.S. patent application Ser. No. 13/194,928, pending, which is a continuation of U.S. patent application Ser. No. 10/772,964, filed Feb. 4, 2004, abandoned, which claims priority to EP Patent Application No. 03025769.5, filed Nov. 11, 2003. The contents of each of the foregoing applications are incorporated herein by reference in their entirety.

FIELD OF THE INVENTION

The present invention relates to a formulation for the controlled release of sexual hormones to the systemic circulation after nasal application.

DESCRIPTION OF THE RELATED ART

Nasal drug delivery offers many advantages that include rapid adsorption due to abundant capillary vessels, fast onset of action, avoidance of hepatic first-pass metabolism, utility for chronic medication and ease of administration.

It is known that, in contrast to large and/or ionized molecules, lipophilic pharmaceutical compounds having a sufficiently low molecular weight in general are readily adsorbed by the mucous membrane of the nose. For such drugs it is possible to obtain pharmacokinetic profiles similar to those obtained after intravenous injection.

However, maintaining constant in vivo therapeutic drug concentrations for an extended period of time has been problematic because of the rapid mucociliary clearance of the therapeutic agent from the site of deposition resulting in a short span of time available for absorption and of the presence of enzymes that may cause degradation in the nasal cavity.

A lot of efforts have been made to overcome these limitations including the use of bioadhesive systems that increase residence time in the nasal cavity, the use of enhancers to improve permeability of the nasal membrane or the use of stabilizers that prevent degradation of drugs.

Thus in GB 1987000012176 the use of bioadhesive microspheres has been proposed by Ilium, and in PCT/GB98/01147 the use of in-situ gelling pectin formulations by WEST Pharmaceuticals.

Investigations on the nasal absorption of sexual steroids, rather small and lipophilic compounds, have shown that they are readily absorbed by the mucous membrane of the nose and are found very quickly in serum. Due to this fact, to the short half-life of the compounds and to limited possibilities for formulating nasal application forms with sustained release their use in clinical practice has been limited up to now because hormone replacement therapy, in general, is a long-term application.

Several formulations were proposed for these drugs. Thus, in the case of testosterone, which is nearly water-insoluble and somewhat better in vegetable oil, Hussain et al., "Testosterone 17β-N,N-dimethylglycinate hydrochloride: A pro-drug with a potential for nasal delivery of testosterone", J. Pharmaceut. Sci. 91(3): 785-789 (2002), concluded that it would be an ideal candidate for nasal administration, if its solubility in water could be increased. He proposed to use a water-soluble pro-drug, testosterone 17β-N,N-dimethylglycinate, and found serum levels equal to intravenous administration with peak plasma concentrations within 12 min (25 mg dose) and 20 min (50 mg dose), respectively, and elimination half-lives of about 55 min. It must be mentioned that this speed is not necessary/desirable because sex hormone replacement is not an emergency therapy.

Ko et al., "Emulsion formulations of testosterone for nasal administration", J. Microencaps., 15(2): 197-205 (1998), proposed the use of charged testosterone submicron O/W emulsion formulations (water/Tween80, soybean oil/Span80) based on the hypothesis that increased absorption is possible upon solubilisation of the drug and/or prolongation of the formulation residence time in the nose. He found a higher relative bioavailability of the positively (55%) and negatively (51%) charged emulsion compared to the neutral one (37%). Tmax was observed in every case at about 20 min after administration. It is difficult to discuss these results because Ko did not take blood samples before application and thus it is not possible to evaluate the differences in the decrease of serum levels, although from a graph it seems that after intravenous application (hydroalcoholic solution) the level shows the longest elimination half time. In practice, however, such an emulsion is not suitable because the droplet size (430 nm) is not acceptable for nasal application.

The solubility of progesterone in water and oil is somewhat comparable to that of testosterone, but investigators have had different approaches:

Cicinelli et al., "Progesterone administration by nasal spray", Fertil Steril 56(1): 139-141 (1991), "Nasally-administered progesterone: comparison of ointment and spray formulations", Maturitas 13(4): 313-317 (1991), "Progesterone administration by nasal sprays in menopausal women: comparison between two different spray formulations", Gynecol Endocrinol 6(4): 247-251 (1992), "Effects of the repetitive administration of progesterone by nasal spray in postmenopausal women", Fertil Steril, 60(6): 1020-1024 (1993) and "Nasal spray administration of unmodified progesterone: evaluation of progesterone serum levels with three different radioimmunoassay techniques", Maturitas 19(1): 43-52 (1994), showed that progesterone, dissolved in almond oil (20 mg/ml) and administered by nasal spray, lead to higher bioavailability than that provided by progesterone dissolved in dimethicone or a PEG-based ointment. After, nasal application of progesterone in almond oil Cmax levels were observed after 30 to 60 minutes, decreasing significantly 6 to 8 hours after single administration.

Steege et al. "Bioavailability of nasally administered progesterone", Fertil Steril, 46(4): 727-729 (1986), dissolved progesterone in polyethylene glycol (200 mg/ml) and found Tmax at 30 min. The duration of serum levels was at least 8 hours but with high variations.

When progesterone was formulated in ethanol/propylene glycol/water however Tmax was only 5.5 min (Kumar et al, "Pharmacokinetics of progesterone after its administration to ovariectomized rhesus monkeys by injection, infusion, or nasal spraying", Proc. Natl. Acad. Sci. U.S.A., 79: 4185-9 (1982)).

Provasi et al., "Nasal delivery progesterone powder formulations comparison with oral administration", Boll. Chim. Farm. 132(10): 402-404 (1993), investigated powder mixtures (co-ground and co-lyophilized progesterone/cyclodextrin) containing progesterone and also found Tmax within 2-5 min and a serum level decrease already in about 20 min.

These results are quite similar to that found for testosterone (see above) and for an already marketed aqueous nasal spray containing estradiol, formulated in cyclodextrin (Aerodiol®). Maximum plasma levels are reached within 10-30 minutes decreasing to 10% of the peak value after 2 hours already. Again, this speed is not necessary for sex hormone replacement therapy and not desirable in view of the short elimination half-time of hormones.

Apart from the "liberation/adsorption" problem shown above, in connection with sexual hormones and bioavailability, nearly exclusively the crucial liver metabolism and the short half-life are discussed, although a problem is also the high protein-binding. Approximately 40% of circulating plasma testosterone e.g. binds to sex hormone binding globulin (SHBG)—in men 2%, in women up to 3% remains unbound (free)—and the remainder binds to albumin and other proteins. The fraction bound to albumin dissociates easily and is presumed to be biologically active, whereas the SHBG fraction is not. The amount of SHBG in plasma however determines the distribution of testosterone in free and bound forms, where free testosterone concentrations determine (limit) the drug's half-life.

Accordingly, there is a constant need for a sexual hormone drug formulation system that is therapeutically effective when administered to the nose of a patient and is safe, stable and easily manufactured.

SUMMARY OF THE INVENTION

The inventor made intensive studies of various sexual hormone drug formulations and, as a result, surprisingly found that the incorporation of the drug into a special lipophilic or partly lipophilic system not only leads to a higher bioavailability in general caused by sustained serum levels in plasma, but also to a more favourable serum level profile.

The invention comprises a formulation for nasal application comprising a) at least one sexual hormone drug; b) at least one lipophilic or partly lipophilic carrier; and c) a compound or a mixture of compounds having surface tension decreasing activity, an amount effective for in situ generation of an emulsion upon contact of the formulation with water.

Preferably, the lipophilic carrier comprises an oil.

More preferably, said oil is a vegetable oil.

Most preferably, said oil is castor oil.

A preferred embodiment of the invention is characterized in that the amount of oil comprises between 30% and 98% by weight, preferably between 60 and 98% by weight, more preferably between 75% and 95% by weight, even more preferably between 85% and 95% by weight and most preferably around 90% by weight of the formulation.

A further embodiment is characterized in that component (c) comprises at least one surfactant selected from the group consisting of lecithin, fatty acid ester of polyvalent alcohols, of sorbitanes, of polyoxyethylensorbitans, of polyoxyethylene, of sucrose, of polyglycerol and/or at least one humectant selected from the group consisting of sorbitol, glycerine, polyethylene glycol, and macrogol glycerol fatty acid ester, or a mixture thereof.

Most preferably, component (c) comprises an oleoyl macrogolglyceride or a mixture of oleoyl macrogolglycerides.

Preferably, component (c) is comprised within the formulation in an amount of from 1 to 20% by weight, preferably 1 to 10% by weight, more preferably 1 to 5% by weight, and most preferably at around 4% by weight.

A further embodiment comprises a viscosity regulating agent.

Preferably, it is preferred that said viscosity regulating agent comprises a thickener or gelling agent selected from the group consisting of cellulose and cellulose derivatives, polysaccharides, carbomers, polyvinyl alcohol, povidone, colloidal silicon dioxide, cetyl alcohols, stearic acid, beeswax, petrolatum, triglycerides and lanolin, or a mixture thereof.

Most preferably, said viscosity increasing agent is colloidal silicon dioxide.

Preferably, the viscosity regulating agent is comprised within the formulation in an amount of from 0.5 to 10% by weight, preferably 0.5 to 5% by weight, more preferably 1 to 3% by weight, and most preferably at around 3% by weight.

In a preferred embodiment, the sexual hormone drug is testosterone.

Preferably, it is preferred that the sexual hormone drug is comprised within the formulation in an amount of from 0.5 to 6% by weight, preferably 2 to 4% by weight, more preferably 0.5 to 2% by weight, and most preferably at around 2% by weight.

BRIEF DESCRIPTION OF THE DRAWING

FIG. 1 shows the serum levels of free testosterone at baseline and after nasal application of testosterone.

DETAILED DESCRIPTION OF THE INVENTION

The resultant formulation is chemically and physically stable and can be a suspension or a solution of the pharmacologically active substance. Preferably it is filled into a preservative-free, airless multi-dose device able to accurately deliver doses of the above formulation, also at higher viscosities.

Once at the absorption site, the drug or the drug particles should be efficiently trapped at the deposition site and be absorbed at a predictable rate across the mucous membrane of the patient, thereby limiting possible deactivation by metabolizing enzymes and/or protein-binding.

As used herein the following terms are defined as follow:

The term "sexual hormone drug" shall mean at least one sexual hormone (such as testosterone) or at least one biologic pro-drug of a sexual hormone (such as androstenedione, progesterone, 17-α-hydroxyprogesterone) or at least one derivative of a sexual hormone (such as mestanolone and 4-chloro-1-dehydromethyltestosterone) or a combination thereof. In a preferred embodiment the sexual hormone drug is testosterone.

The sexual hormone drug is comprised within the formulation in an amount of from 0.5 to 6% by weight, preferably 2 to 4% by weight, more preferably 0.5 to 2% by weight, and most preferably at around 2% by weight The drug of this invention may be introduced into the formulation also in a processed form such as microspheres, liposomes etc.

The term "lipophilic carrier" shall comprise, but not limited to, a vegetable oil such as castor oil, soybean oil, sesame oil or peanut oil, fatty acid ester such as ethyl- and oleyloleat, isopropylmyristate, medium chain triglycerides, glycerol esters of fatty acids, or polyethylene glycol, phospholipids, white soft paraffin, or hydrogenated castor oil. Particularly useful is castor oil.

The incorporation of the drug is also possible into an oil mixture.

The particular amount of oil that constitutes an effective amount is dependent on the particular viscosity regulating agent (see below) used in the formulation. It is therefore not practical to enumerate specific amounts for use with specific formulations of the invention. Generally, however, the lipophilic part can be present in a formulation in an amount between 30% and 98% by weight, preferably between 60 and 98% by weight, more preferably between 75% and 95% by weight, even more preferably between 85% and 95% by weight and most preferably around 90% by weight of the formulation.

Component (C) shall comprise at least a surfactant such as, but not limited to, lecithin, fatty acid ester of polyvalent alcohols, of sorbitanes, of polyoxyethylensorbitans, of polyoxyethylene, of sucrose, of polyglycerol and/or at least one humectant such as sorbitol, glycerine, polyethylene glycol, or macrogol glycerol fatty acid ester. Particularly useful, however, are oleoyl macrogolglycerides (such as Labrafil M 1944 CS, as available from Gattefossé (Franco)).

The incorporation of the drug is also possible into a surfactant mixture.

The particular amount of surfactant that constitutes an effective amount is dependent on the particular oil or oil mixture (see above) used in the formulation. It is therefore not practical to enumerate specific amounts for use with specific formulations of the invention. Generally, however, the surfactant can be present in a formulation in an amount of from 1 to 20% by weight, preferably 1 to 10% by weight, more preferably 1 to 5% by weight, and most preferably at around 4% by weight.

The term "viscosity regulating agent" shall mean a thickener or gelling agent. Examples are, but not limited to, cellulose and derivatives thereof, polysaccharides, carbomers, polyvinyl alcohol, povidone, colloidal silicon dioxide, cetyl alcohols, stearic acid, beeswax, petrolatum, triglycerides or lanolin. Particularly useful however is colloidal silicon dioxide (such as Acrosil 200, as available from Degussa).

The incorporation of the drug is also possible into a mixture of thickeners or gelling agents.

The particular amount of thickener/gelling agent that constitutes an effective amount is dependent on the particular oil or oil mixture (see above) used in the formulation. It is therefore not practical to enumerate specific amounts for use with specific formulations of the invention. Generally, however, the thickener/gelling agent(s) can be present in a formulation in an amount from 0.5 to 10% by weight, preferably 0.5 to 5% by weight, more preferably 1 to 3% by weight, and most preferably at around 3% by weight.

The formulation according to this invention may also be processed into powder form, e.g. by lyophilization or spray-drying.

Generally the formulations of the invention can be prepared very easily by conventional methods, i.e.:

Emulsion

The thickener or gelling agent is added to a sufficient amount of water and dispersed with high speed mixing and, if necessary, a surfactant (mixture 1). In a second container water and/or the lipophilic carrier are introduced and, if necessary, a surfactant (mixture 2). To mixture 2 the hormone is added very carefully avoiding introducing air. Mixture 2 is added to mixture 1, if necessary pH and tonicity are adjusted and the final mixture is homogenised and sterilised.

Water-Free Formulation

Lipophilic carrier and emulsifier are filled into a stirrer vessel and about 75% of the viscosity regulating agent is mixed in. The hormone is added under stirring until a homogenous dispersion of the active ingredient is obtained. Then the formulation is adjusted to the necessary viscosity with the rest of the viscosity regulating agent.

The formulation is preferably filled into a preservative-free, airless nasal spray device such as the COMOD system available from Ursatec.

By "higher availability" is meant that after a single application a serum level of sexual hormone significantly higher than baseline is maintained for 6 hours, more preferably for 8 hours and most preferably for at least 10 hours.

Because sexual hormones are nearly not soluble in water liberation from the formulation is the speed-limiting step for adsorption. It has been surprisingly found that the incorporation of a sexual hormone drug such as testosterone in an oily formulation containing a suitable surfactant according to the invention leads of to physiologic serum levels and to a steady, sustained action of the hormone over time.

On one hand, the release of the hormone is sustained due to its solubility in the oily carrier and to the viscosity of the formulation remaining on the mucous membrane for a prolonged duration of time.

On the other hand, upon contact of the formulation with the humidity of the mucous membrane the drug's precipitation is hindered by the surfactant's property to form oil drops containing the drug. Thus by adding a suitable surfactant to the formulation the dissolution pattern of the hormone becomes more favourable and effective because there is no big variability in dissolution ensuring bioequivalence.

EXAMPLE

Typical Formulation

The formulation shown below was selected considering the serum level of the active ingredient achieved but it also exhibits a skin care property which is important for long term applications.

TABLE 1

Most preferred formulation

| Compound | Amount per container | Delivery per spray |
|---|---|---|
| Testosterone | 2% | ≈2.8 mg |
| Aerosil ® 200 | 3% | ≈4.2 mg |
| Labrafil ® M 1944 CS | 4% | ≈5.6 mg |
| Castor oil, refined grade | 91% | ≈127.4 mg |

Typical Serum Level

Comparing different formulations (see FIG. 1) containing testosterone it is obvious that Cmax is clearly decreased in the special oily formulation of this invention, which is desirable in view of toxicological considerations. Further the level of unbound testosterone is very constant over at least 10 hours mimicking the physiologic daily rhythm of testosterone release.

The dotted line shows the serum level after application of 1 spray per nostril once of the most preferred formulation (see Table 1).

It can be concluded that the formulation for nasal application of this invention is different from conventional formulations, especially to those for sustained release, as it is mimicking the physiologic daily rhythm of testosterone release. It is also avoiding supra- and sub-normal testosterone levels, which is pleasant for the patient and a demand for hormone replacement therapy. As shown in FIG. 1 (upper line), a simple nasal spray containing testosterone is unsatisfactory in this sense.

The features disclosed in the foregoing description, in the claims and/or in the drawings may, both separately and in any combination thereof, be material for realising the invention in diverse forms thereof.

The invention claimed is:

1. A method of treating a patient in need of testosterone replacement therapy with a testosterone nasal gel, said method comprising:
   administering a testosterone gel to the nasal mucosa of each nostril of a patient in need of testosterone replacement therapy, wherein the testosterone is present within the testosterone gel in an amount of from about 0.5% to about 6% by weight of the testosterone gel, for delivering testosterone to the nasal mucosa to treat the patient in need of testosterone replacement therapy with testosterone;
   wherein, an elevated testosterone serum level in the patient is achieved following said nasal administration of the testosterone gel to the nasal mucosa of the patient; and
   wherein, the achieved testosterone serum level in the patient is maintained above the patient's testosterone baseline for at least 6 hours following said nasal administration of the testosterone gel.

2. The method of claim 1, wherein the testosterone gel is provided in a device capable of dispensing multiple, individual doses of the testosterone gel to the nasal mucosa of each nostril.

3. The method of claim 1, wherein the testosterone gel provides for the controlled release of testosterone into systemic circulation after nasal application.

4. The method of claim 1, wherein the testosterone gel provides for sustained serum levels of testosterone.

5. The method of claim 1, wherein the testosterone gel provides for the controlled release of testosterone into the brain after nasal application.

6. The method of claim 1, wherein the serum level is achieved after one said administration of the testosterone gel per nostril.

7. The method of claim 6, wherein the serum level of unbound testosterone is similar to the physiologic daily rhythm of testosterone release.

8. The method of claim 1, wherein said testosterone is maintained at a serum level greater than baseline for at least about 8 hours after nasal administration.

9. The method of claim 1, wherein said testosterone is maintained at a serum level greater than baseline for at least about 10 hours after nasal administration.

10. The method of claim 1, wherein said testosterone is present within the testosterone gel in an amount of from about 2% to about 4% by weight of the testosterone gel.

11. The method of claim 1, wherein said testosterone is present within the testosterone gel in an amount of from about 0.5% to about 2% by weight of the testosterone gel.

12. The method of claim 1, wherein said testosterone is present within the testosterone gel in an amount of about 2% by weight of the testosterone gel.

13. A method for nasally treating a patient in need of testosterone replacement therapy with testosterone, said method comprising:
   applying a testosterone oleogel to nasal mucosa in each nostril of a patient in need of testosterone replacement therapy for controlled release of testosterone for nasally treating the patient with testosterone;
   wherein, the testosterone is present within the testosterone oleogel in an amount of from about 0.5% to about 6% by weight of the testosterone oleogel for delivering testosterone to treat the patient in need of testosterone replacement therapy;
   wherein, an elevated testosterone serum level in the patient is achieved following said application of the testosterone oleogel to the nasal mucosa of the patient; and
   wherein, sustained serum levels of testosterone are maintained in the patient for at least 6 hours following said nasal administration of the testosterone oleogel to the nasal mucosa of the patient.

14. The method of claim 13, wherein the testosterone oleogel is provided in a device capable of dispensing multiple individual doses of the testosterone oleogel to the nasal mucosa of each nostril multiple.

15. The method of claim 13, wherein the testosterone oleogel provides for the controlled release of testosterone into systemic circulation after the nasal application.

16. The method of claim 13, wherein the testosterone oleogel provides for the controlled release of testosterone into the brain after nasal application.

17. The method of claim 13, wherein the serum level is achieved after one said application of the testosterone oleogel per nostril.

18. The method of claim 13, wherein the serum level of unbound testosterone is similar to the physiologic daily rhythm of testosterone release.

19. The method of claim 13, wherein said testosterone is maintained at a serum level greater than baseline for at least about 8 hours after said nasal administration of the testosterone oleogel.

20. The method of claim 13, wherein said testosterone is maintained at a serum level greater than baseline for at least about 10 hours after said nasal administration of the testosterone oleogel.

21. The method of claim 13, wherein said testosterone is present within the testosterone oleogel in an amount of from about 2% to about 4% by weight of the testosterone oleogel.

22. The method of claim 13, wherein said testosterone is present within the testosterone gel formulation in an amount of from about 0.5% to about 2% by weight of the testosterone oleogel.

23. The method of claim 13, wherein said testosterone is present within the testosterone gel formulation in an amount of about 2% by weight of the testosterone oleogel.

* * * * *